United States Patent
Reboni et al.

(10) Patent No.: US 7,648,275 B2
(45) Date of Patent: Jan. 19, 2010

(54) METHOD OF CALIBRATION OF DIGITAL X-RAY APPARATUS AND ITS EMBODIMENTS

(75) Inventors: Voldemar O. Reboni, St. Petersburg (RU); Vitaly V. Jurenja, St-Petersburg (RU); Andrei O. Schiriy, Resp. Mary-El (RU)

(73) Assignee: ZAO "Impulse", St. Petersburg (RU)

( * ) Notice: Subject to any disclaimer, the term of this patent is extended or adjusted under 35 U.S.C. 154(b) by 0 days.

(21) Appl. No.: 12/398,291

(22) Filed: Mar. 5, 2009

(65) Prior Publication Data

US 2009/0161834 A1 Jun. 25, 2009

Related U.S. Application Data

(63) Continuation of application No. PCT/RU2008/000308, filed on May 19, 2008.

(30) Foreign Application Priority Data

Oct. 31, 2007 (RU) ............................... 2007140023

(51) Int. Cl.
*G01D 18/00* (2006.01)
(52) U.S. Cl. ..................................... 378/207
(58) Field of Classification Search ................. 378/162, 378/207
See application file for complete search history.

(56) References Cited

U.S. PATENT DOCUMENTS 5,442,674 A    8/1995    Picard et al.
5,636,255 A *    6/1997    Ellis .............................. 378/20

(Continued)

FOREIGN PATENT DOCUMENTS

AT         377 689         4/1985

(Continued)

OTHER PUBLICATIONS

International Search Report, mailed Oct. 16, 2008, from International application No. PCT/RU2008/000308, filed May 19, 2008.

(Continued)

*Primary Examiner*—Allen C. Ho
(74) *Attorney, Agent, or Firm*—Houston Eliseeva LLP

(57) ABSTRACT

The inventions (variants) are intended for improvement of calibration precision of digital X-ray apparatuses: computed tomographs, as well as digital X-ray apparatuses equipped with C-arm and U-arm type stands, which method is based on calculation of mechanical instability of the stand. Calibration method for X-ray apparatus, in which one or two X-ray contrast balls of different diameters are placed in the scanning field, excluding its centre, a series of images of the scanning field with different angles of the stand rotation are obtained, the X-direction and Y-direction regular components of mechanical instability of the X-ray apparatus stand are determined using the coordinates of projection centre of the ball, X-direction and Y-direction calibration modifications set for mechanical instability of the stand are formed, which modifications are used for correction of the images, according to the invention the additional regular component of mechanical instability of digital X-ray stand is determined using the scales of projections, and the calibration data set for mechanical instability of the stand, which includes the scale calibration modifications, is formed.

2 Claims, 6 Drawing Sheets

U.S. PATENT DOCUMENTS

| | | | |
|---|---|---|---|
| 5,822,396 A | 10/1998 | Navab et al. | |
| 6,081,577 A * | 6/2000 | Webber | 378/23 |
| 6,120,180 A | 9/2000 | Graumann | |
| 6,243,439 B1 * | 6/2001 | Arai et al. | 378/20 |
| 6,466,638 B1 * | 10/2002 | Silver et al. | 378/4 |
| 6,652,142 B2 * | 11/2003 | Launay et al. | 378/205 |
| 6,731,283 B1 * | 5/2004 | Navab | 345/424 |
| 7,016,456 B2 | 3/2006 | Basu et al. | |
| 7,311,440 B2 * | 12/2007 | Yoon et al. | 378/207 |
| 2001/0053204 A1 | 12/2001 | Navab et al. | |

FOREIGN PATENT DOCUMENTS

RU 47 536 U1 8/2005

OTHER PUBLICATIONS

Fahrig, R. et al., "Three-dimensional computed tomographic reconstruction using a C-arm mounted XRII: Image-based correction of gantry motion nonidealities," Med. Phys. 27 (1), Jan. 2000, pp. 30-38.

* cited by examiner

METHOD OF CALIBRATION OF DIGITAL X-RAY APPARATUS AND ITS EMBODIMENTS

RELATED APPLICATIONS

This application is a Continuation of PCT application serial number PCT/RU2008/000308, filed on May 19, 2008, which claims priority to Russian Patent Application No. 2007140023, filed on Oct. 31, 2007, both of which are incorporated herein by reference in their entirety.

FIELD OF THE INVENTION

The group of inventions belongs to medical X-ray engineering, namely to the check and measurement instruments for technical characteristics of digital X-ray apparatuses: computed tomographs as well as digital X-ray apparatuses equipped with C-arm and U-arm type stands.

BACKGROUND OF THE INVENTION

The principal purpose of digital X-ray apparatus calibration is a production of highest quality images of the object under examination (patient) in course of radiological exploration. The quality of the explorative images is highly influenced by mechanical instability of the X-ray computed tomograph stand (also known as tomograph gantry) and of the C-arm and U-arm stands of the digital X-ray apparatuses. So for example, the changes in digital X-ray apparatus stand rotation path may result in failures of the preliminary calibrations of the detector, such as calibration of shading, etc. For the computed tomography apparatuses, besides the failure of the detector preliminary calibrations, even smallest changes in the path of the tomographic scanning may result in considerable deterioration of an image being reconstructed. The mechanical instability of the computed X-ray tomograph stand, of the C-arm and U-arm stands of digital X-ray apparatuses includes regular and random components. The invention under application is designed for accurate correction of the images obtained with use of X-ray apparatuses with due account of the regular component of the mechanical instability of the digital X-ray apparatus stand.

The following calibration methods of the mechanical instability of the X-ray apparatuses with the C-arm stand, in which the external monitoring systems of the apparatus mechanical instability are applied, are known:

a) It is known the method [Application for a patent USA No. 2001053204, publ. 20 Dec. 2001, IPC A61B6/00], according to which a special marker is installed onto X-ray tube and, with use of an external optical stereo camera, which is not connected to the X-ray apparatus, the rotation path of the apparatus is being tracked; the required corrections for the apparatus mechanical instability are determined regarding the path.

The obstacles to achieve the said below technical result, when using the known method, include, besides the complexity and the expensiveness of the given method application, possible obstructing of the optical stereo camera field of view (the marker becomes invisible for the camera during the apparatus rotation when the patient's table stands between the camera and the marker or when a medical staff person intrudes into the camera field of view, etc.) Thus, a part of diagnostic data will be obtained without corrections for mechanical instability of the apparatus, which circumstance leads to deterioration of the X-ray images being obtained.

b) It is known the method [U.S. Pat. No. 6,120,180, publ. 19 Sep. 2000, IPC A61B6/00], according to which ultrasonic emitters are mounted onto X-ray tube and X-ray detector, the emitters signals are registered by means of at least two ultrasonic receivers. The signals received by the ultrasonic detectors are processed and the rotation path of the apparatus is determined using them; the corrections for mechanical instability of the apparatus are determined regarding the path.

The obstacles to achieve the said below technical result, when using the known method, include, besides the complexity and the expensiveness of the given method application, the fact that the ultrasonic radiation characteristics depend on the temperature of the medium through which it propagates. This leads to necessity of complex calculations and correction of the information received by the ultrasonic data receivers, because the temperatures of X-ray tube, X-ray sensor and the ambient air are different.

It is known the calibration method for computed X-ray tomograph [U.S. Pat. No. 5,822,396, publ. 13 Oct. 1998, IPC A61B6/00], according to which test objects are placed into the scanning field for each exposure of the object under examination (a patient, when the X-ray apparatus is used in medicine). The divergences between the observed and ideal positions let calculate displacement data for each roentgenogram, which data are used for real time compensation of the stand mechanical instability.

The obstacles to achieve the said below technical result, when using the known method include the fact, that the test objects of this method are made of X-ray contrast material, of a metal as a rule. Presence of such objects during each exposure causes the formation of artifacts on the image being reconstructed; that leads to inaccuracies when X-ray tomographic examining.

The same purpose method most close to the both variants of the invention under application regarding its technical essence is calibration method for computed X-ray tomograph given in [Fahrig R., Holdsworth D. W., Three-dimensional computed tomographic reconstruction using a C-arm mounted XRII: image-based correction of gantry motion nonidealities. Medical Physics, 2000, V. 27(1), c. 30-38.]. The method includes obtaining of preliminary calibration data for regular component of the mechanical instability of X-ray apparatus stand using a steel ball (or several balls) installed in the scanning field of X-ray apparatus. The method implies obtaining of a series of N roentgenograms for different the stand rotation angles $\phi_i$. The roentgenograms are obtained and processed in digital form. In each roentgenogram, the ball (or several balls) projection centre coordinates are to be found. Using the found coordinates, the regular component of the X-ray apparatus stand mechanical instability is determined. In the method, the leading role belongs to X-direction and Y-direction calibration data of X-ray apparatus stand mechanical instability, the obstacles to achieve the said below technical result using the known method include the fact, that in the known method the regular component of digital X-ray apparatus stand, Z-direction mechanical instability (scale calibration data) is not determined. The scale calibration data are relatively small in absolute values, although in case of the focus distance of 1200 mm and the object under examination size of 100 mm, the Z-direction shift by 10 mm causes change of the object under examination projection size by 1.7% (if the object under examination is located in the middle between the X-ray tube and the detector), that is inappropriate in the examinations, where high precision of measurements is needed (computerized tomography, vessels prosthetics angiography, etc.), The said Z-direction component of the stand mechanical instability (influencing the scale) may lead to error during the X-direction and Y-direction calibration data determination.

SUMMARY OF THE INVENTION

The objective of the invention is to create higher precision calibration method for X-ray apparatuses. The technical result of the invention according to the first and the second variants is the improvement of digital X-ray apparatus calibration precision due to formation of the calibration data set for the stand regular component of mechanical instability with due account of the scale calibration data, and the increasing of mechanical precision tolerance of the X-ray apparatus stand rotation, in case of using the methods under application. In the second variant, the determination precision of calibration data for the mechanical instability regular component of X-ray apparatus is higher than the precision in the first one due to the use, during calibration, of at least two balls of different diameters. The application of calibration data to X-ray images reduces the image noise that in its turn improves the resolution of low-contrast and high-contrast roentgenograms of X-ray apparatus, owing to what, in the medical X-ray diagnostics, for example, it is possible to detect malignant neoplasms at an earlier stage.

In the first variant of the invention, the said technical result is achieved due to the fact, that in the calibration method for digital X-ray apparatus, which implies that in the scanning field excluding its centre at least one X-ray contrast ball is installed, the scanning field images are obtained, the X-direction and Y-direction regular components of the mechanical instability of the stand are determined by the coordinates of the projection centre of the ball, a set of calibration data of X-direction and Y-direction mechanical instability of the stand, which are used for modification of the images according to the invention, is formed, and then in addition, scale regular component of the mechanical instability of digital X-ray apparatus stand is determined (scale coefficient SK), and a set of calibration data of mechanical instability of the stand which includes the X-direction, Y-direction and scale calibration data, is formed.

In the second variant of the invention, the said technical result is achieved due to use of digital X-ray apparatus calibration method, which implies that X-ray contrast balls are placed into the scanning field, excluding its centre, the scanning field images are obtained, regular components of the mechanical instability of the stand are determined using the coordinates of the projection centre of the balls, the set of X-direction and Y-direction calibration data used for correction of the images, in accordance with the invention, at least two X-ray contrast balls of different diameters are placed into the scanning field, the X-direction and Y-direction regular components of mechanical instability of digital X-ray apparatus stand are determined using the coordinates of projection centre of the ball of lower diameter, whereas the scale regular component of mechanical instability of digital X-ray apparatus stand (scale coefficient SK) is determined using the coordinates of projection centre of the ball of higher diameter, and a set of calibration data for mechanical instability of the stand, which is based on the obtained X-direction, Y-direction and scale data, is formed.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
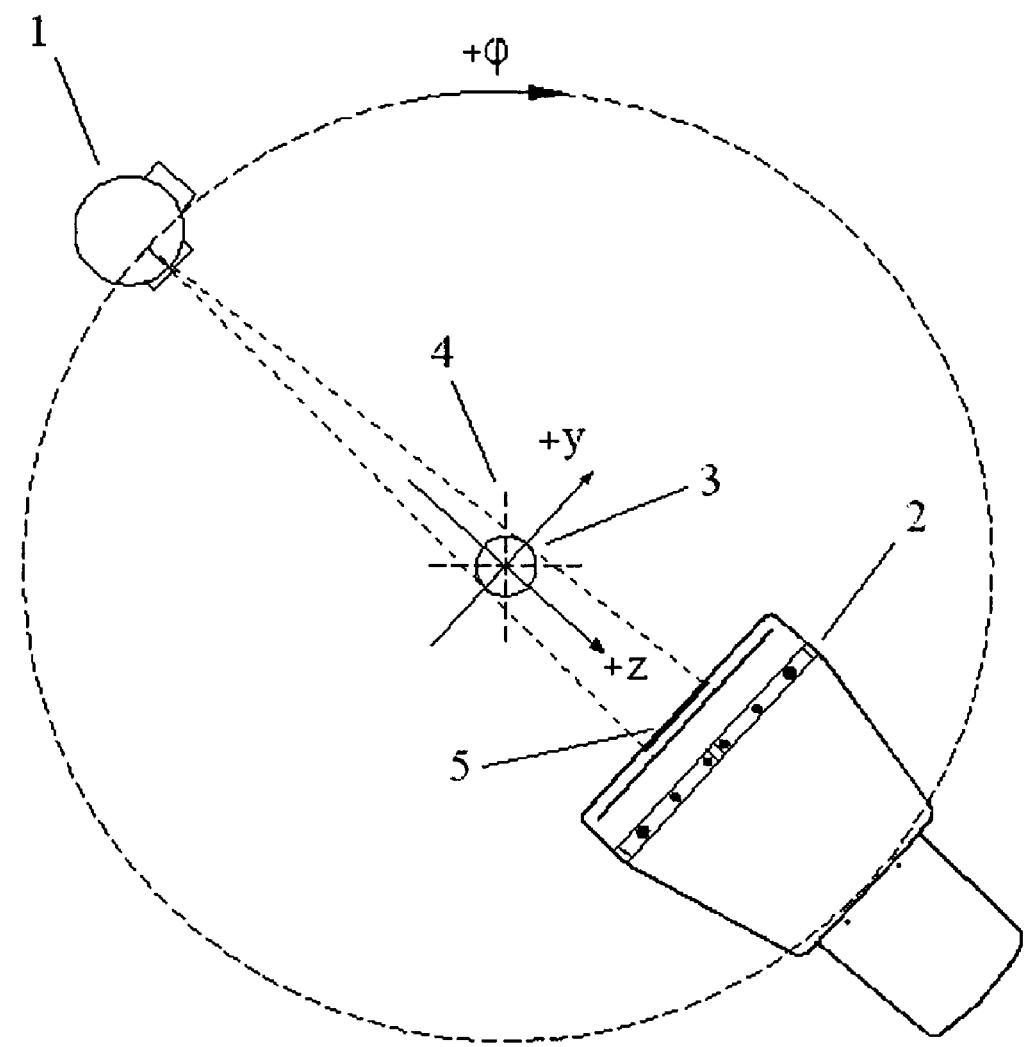
FIG. 1 Layout of digital X-ray apparatus (view along the axis X).
Figure 2:
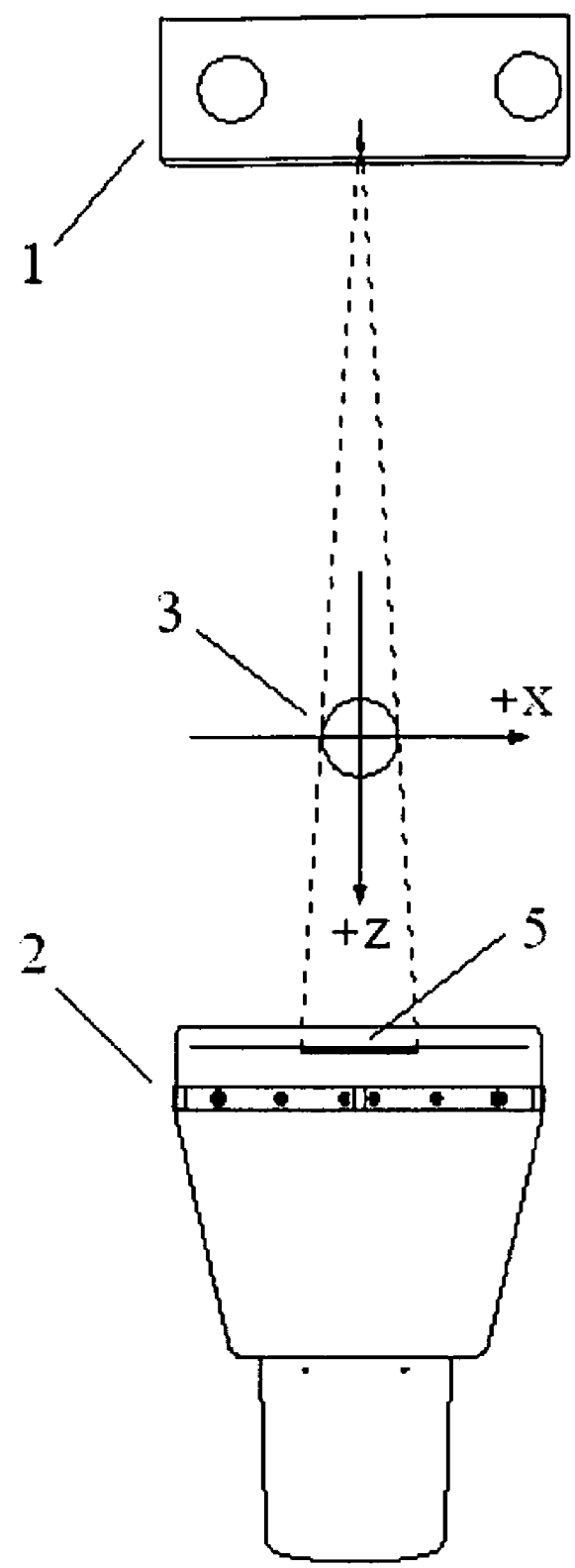
FIG. 2 Layout of digital X-ray apparatus (view along the axis Y).

The method according to the first variant of the invention is to be implemented by means of device (FIG. 1, 2). The FIG. 1, 2 schematically shows the layout of digital X-ray apparatus, where:

1—X-ray tube,
2—detector,
3—ball of X-ray contrast material,
4—centre of the scanning path,
5—projection of the ball of X-ray contrast material.

In the second variant at least two balls made of X-ray contrast material, for example of steel, of different diameters, placed in the scanning field, excluding its centre are used as a calibration object.

The preliminary calibration of digital X-ray apparatus stand which includes X-ray tube 1 and detector 2 according to the first variant of the invention is to be implemented the following way. The ball 3 of X-ray contrast material, for example from steel, is placed in the scanning field excluding its centre 4 (the precision of the ball fabrication shall be higher than the spatial resolution of the digital X-ray apparatus.). A series of N roentgenograms with different angles of rotation of the stand $\phi_i$ is obtained. The roentgenograms are obtained and processed in digital form. In each roentgenogram, the centre coordinates of the ball projection 5 and the projection diameter of the ball projection 5 are to be found. This way numerical sequence for each coordinate of the projection centre of the ball, which depends on the stand rotation angle $\phi$, is obtained: $BX(\phi_i)$, $BY(\phi_i)$; $0° \leq \phi_i < 360°$; $i=1 \ldots N$; in order to calculate numerical sequence of the scale coefficient, the numerical sequence $BD(\phi_i)$—of projection diameter of the ball, which depends on the stand rotation angle $\phi_i$, is obtained.

Each numerical sequence $BX(\phi_i)$, $BY(\phi_i)$, $BD(\phi_i)$ may be represented as sum three terms (shown for X, for Y and D—similarly):

$$BX(\phi_i)=BX_{sin}(\phi_i)+BX_{reg}(\phi_i)+ns,$$

where $BX_{sin}(\phi_i)$ is a periodic component, arising from the ball placement outside the centre; $BX_{sin}(\phi_i)=a\cdot\sin(\phi_i+b)+c$; for the interval of angles $0°\leq\phi_i<360°$ lays in one full period;

$BX_{reg}(\phi_i)$ is a regular component;

ns is a random component.

Figure 3:
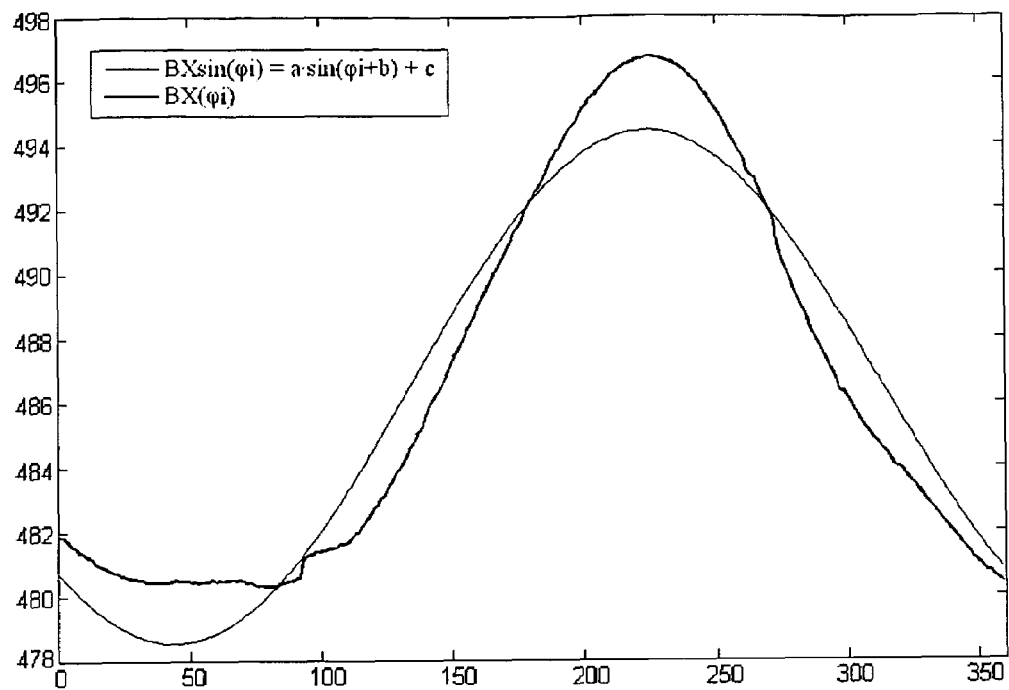
FIG. 3 Numerical sequence of the X-coordinate of the projection centre of the ball and its best approximating sinusoid.
Figure 4:
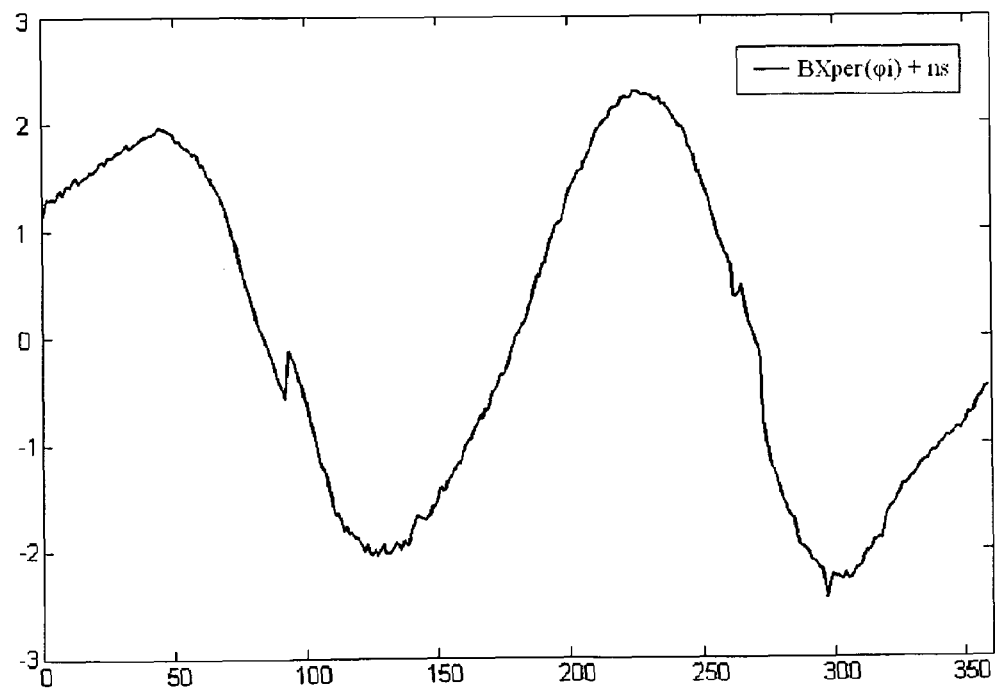
FIG. 4 X-direction regular component of mechanical instability of digital X-ray apparatus stand.

In order to eliminate the periodical component $BX_{sin}(\phi_i)$, parameters a,b,c are found using least-squares method that gives approximation in the sinusoid form (FIG. 3). Median filtering of numerical sequences before approximation is used to eliminate overshootings (rough errors). Then, the values of the found function are subtracted from the original numerical sequence (not filtered with median filter) in corresponding points that allows to obtain (FIG. 4)

$$SX(\phi_i)=BX(\phi_i)-BX_{sin}(\phi_i)=BX_{reg}(\phi_i)+ns.$$

Figure 5:
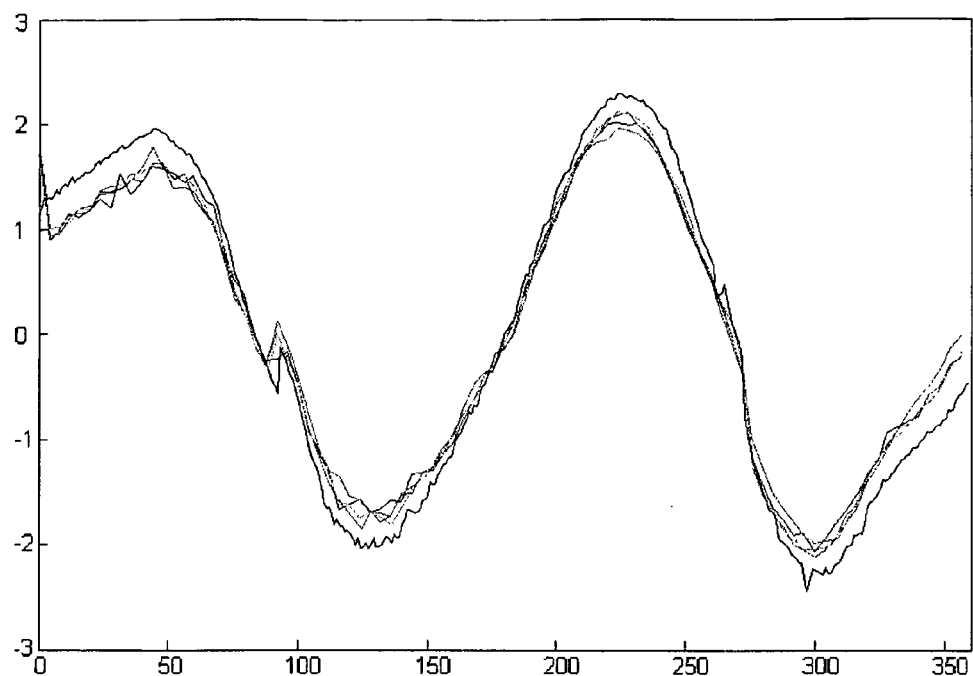
FIG. 5 Set of 5 calculated X-direction regular components of mechanical instability of digital X-ray apparatus stand.

The described process of calibration is repeated K times, which gives a set $SX_j(\phi_i)$, $j=1\ldots K$ (FIG. 5). Averaging of $SX_j(\phi_i)$ at the corresponding values of the angles $\phi_i$, allows to reduce the random component ns and to obtain the estimation of $BX_{reg}(\phi_i)$.

In the second variant, the preliminary calibration of digital X-ray apparatus stand is implemented using at least two X-ray contrast balls of different diameters (the precision of the balls fabrication shall be higher than the spatial resolution of the digital X-ray apparatus.) Estimation of calibration data of the regular component of mechanical instability of X-ray apparatus is obtained according to the first variant of the invention, although the X-direction and Y-direction calibration data are estimated using projection of the ball of smaller diameter, whereas the scale calibration data are estimated using projection of the ball of bigger diameter. For calibration of the regular component of X-direction and Y-direction mechanical instability of digital X-ray apparatus stand it is desired to have a small dimensions of the ball, because the bigger is the ball, the bigger is the deviation of projection centre of the ball from the centre of the ball projection, that leads to reduction of precision of the X-direction and Y-direction calibration data. For the scale calibration of the regular component of mechanical instability of digital X-ray apparatus stand, on the contrary, it is desired that the ball projection would bigger, because the relative deviation of the stand, owing to which the projection diameter changes, decreases, and, therefore, the precision of determination of the scale calibration data raises.

Figure 6:
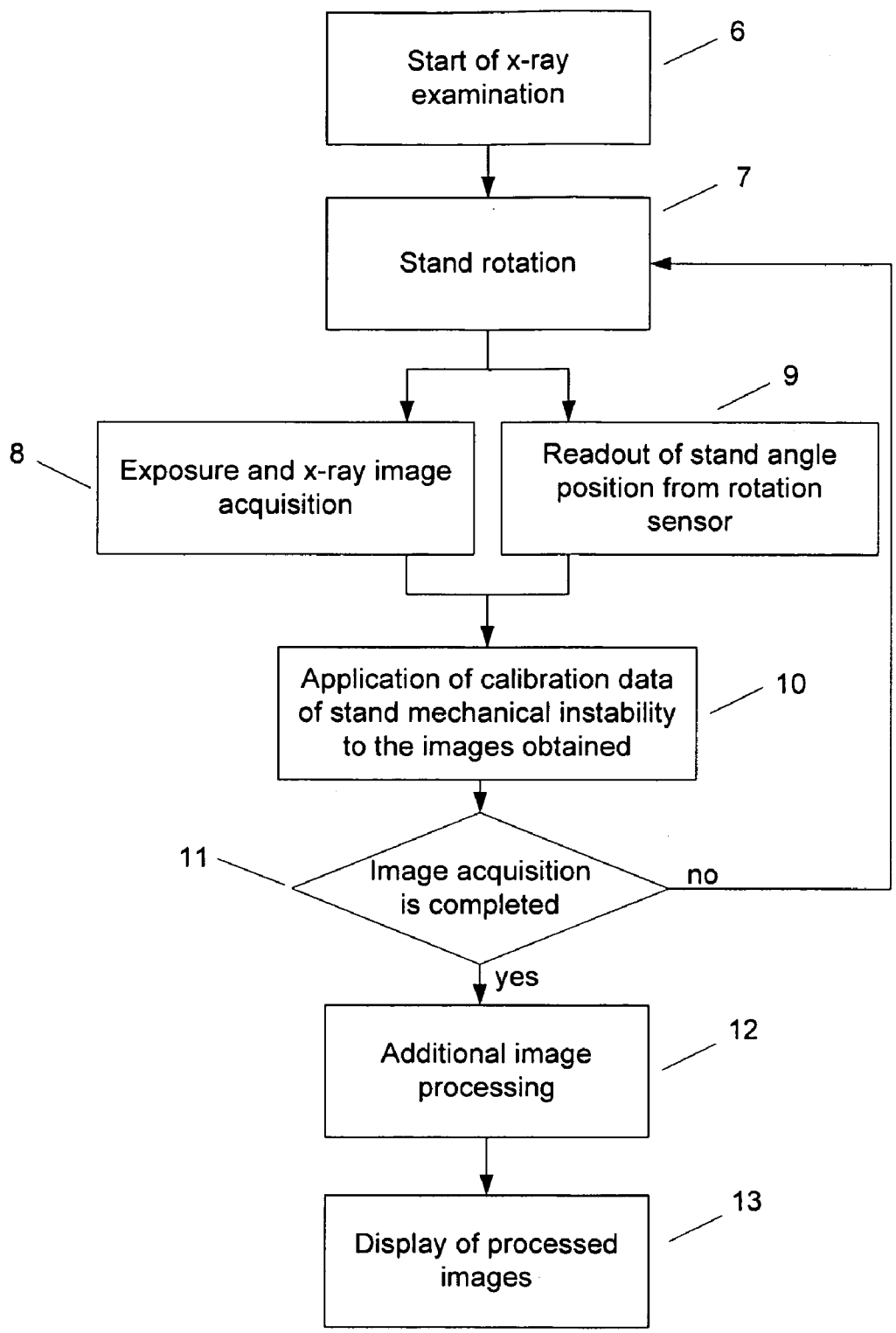
FIG. 6 Flow scheme of the X-ray images correction using the calibration data obtained according to the method variants under application.

Execution of X-ray images correction using the calibration data obtained by the method variants under application is explained by the flow scheme in FIG. 6, where 6—start of X-ray examination, 7—stand rotation, 8—exposure and X-ray image acquisition, 9—readout of stand angle position from rotation sensor, 10—application of calibration data of regular component of stand mechanical instability to the images obtained, 11—image acquisition is completed, 12—additional image processing, 13—displaying of processed images.

In the start of X-ray examination 6, the stand is rotated into the desired position 7, the exposure and the X-ray image of the object under examination is acquired 8, the stand position angle is taken from the rotation sensor 9, the calibration data of the regular component of mechanical instability of the stand 10 that correspond to the given angle of the stand are applied to the obtained images, in case of obtaining of the required number of images 11 the supplementary processing of the images 12 is realized and displayed at the screen 13, otherwise, the operations are repeated since p. 7.

Figure 7:
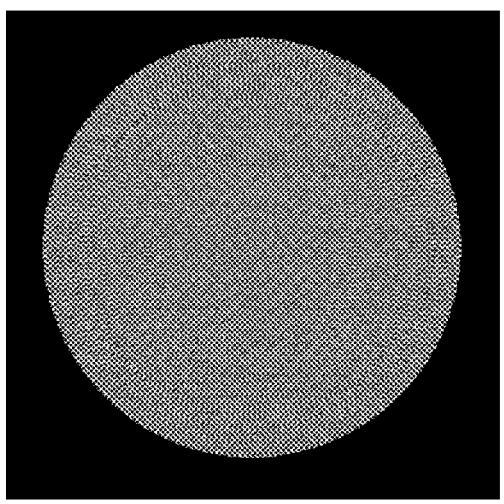
FIG. 7 Reconstruction of uniform mathematical phantom (of the test object) obtained on the basis of the data without Z-direction mechanical instability of the stand.
Figure 8:
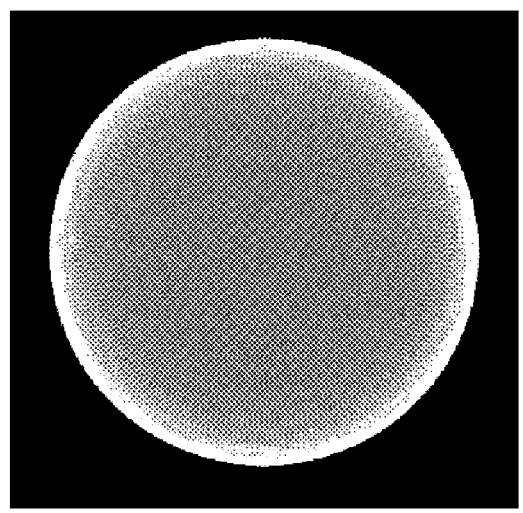
FIG. 8 Reconstruction of uniform mathematical phantom obtained in course of artificial modification of the projections scale commensurate with shift of the stand along the axis Z by 1 cm.

We have demonstrated that the stand deviation along the axis Z influencing the projection scale makes changes to the image being reconstructed, that image was obtained by means of computed tomographs, and also to the images obtained by means of digital X-ray apparatuses with the C-arm and U-arm stands, owing to what the diagnostics capacities of the digital X-ray apparatus are being deteriorated. Application of calibration data of regular component of mechanical instability of the X-ray apparatus stand more concerns to the computed X-ray tomographs, because for the said apparatuses the stand deviation along the axis Z makes more important changes to the image being reconstructed. In FIG. 7, the reconstruction of uniform mathematical phantom (of the test object) that is obtained on the basis of data without mechanical instability of the stand along the axis Z is shown. In FIG. 8, the reconstruction of uniform mathematical phantom obtained in course of artificial modification of the projections scale commensurate with the divergence of the stand along the axis Z for 1 cm is shown. In FIG. 8 we can see that the scale instability makes important changes to the image being reconstructed, increases the image noise and adds supplementary artifacts to the image, which in their turn deteriorate the diagnostics capacities of the computed X-ray tomograph.

This way, improvement of calibration precision for digital X-ray apparatus is achieved due to formation of calibration data set for regular component of mechanical instability of the stand due to taking in account the scale calibration data. In the second variant, the precision of the calibration data of the regular component of mechanical instability of the stand of digital X-ray apparatus is improved in comparison with the first one, what happens due to the use of at least two balls of different diameters in course of the calibration.

Application of calibration data obtained according to the first and the second methods improves low-contrast and high-contrast resolution of the X-ray apparatus, owing to what, for example, in the medical X-ray diagnostics it is possible to detect malignant neoplasms at an earlier stage. Implementation of the methods under application lets reduction of requirements to the mechanical precision of X-ray apparatus stand rotation together with the simultaneous improvement of the reconstructed images quality.

Variants of the Inventions Implementation.

The preliminary calibration of digital X-ray apparatus stand, which includes the X-ray tube 1 and the detector 2 according to the first variant of the invention was realized in the following way. Steel ball of diameter 50 mm was placed into the scanning field (upon a radio transparent support), such a way that the ball image on the roentgenogram (side projection) was a little shifted from the centre.

When roentgenograming, matrix of resolution of 1024× 1024 pixels was used, voltage of the X-ray tube was of 100 kV, the quantity of electricity was of 1 mAs; high frequency generator of power of 80 kW was used; the focal spot of the tube was of 1 mm, the focal distance of the stand was of 1200 mm; the collimator was opened according to the detector dimensions (400×400 mm at the focal distance of 1200 mm).

Series of roentgenograms (360 roentgenograms) was made for different angles of rotation of the stand—from 0 to 360 degrees, the rotation step was of 1 degree approximately (more or less than 1 degree), when the accurate value of rotation angle was taken by means of the sensor of rotation angle. In each roentgenogram of the obtained series, by means of computer processing circle image of the ball was identified and the coordinates of the centre (x, y) and the diameter of this circle were calculated. The obtained numerical sequence for the coordinate X (depending on the angle) is shown in FIG. 3 with the thick line. Then, using the method described in the application, scale, X-direction and Y-direction regular components of mechanical instability of digital X-ray apparatus stand were determined, and after that, the scale, X-direction and Y-direction calibration data set for mechanical instability of the stand to being used for correction of images, according to the invention, were determined as well.

The results of the specific example of calibration realization according to the first variant (method 1) are given in FIG. 3-5, where angle of rotation of the stand $\phi$ goes along the horizontal axis, the value in pixel goes along the vertical one; in FIG. 3, the thick line shows the dependence $BX(\phi)$, the thin line shows the found $BX_{sin}(\phi)$; FIG. 4 shows its difference $SX(\phi)$; FIG. 5 shows the set $SX_j(\phi)$. The values of the scale coefficient $SK(\phi_i)$ are obtained based on the numerical sequence $BD_{reg}(\phi_i)$ that is a regular component of the changes of projection diameter of the ball.

In the second variant under application, the preliminary calibration of the digital X-ray apparatus stand is realized by means of at least two X-ray contrast balls of different diameters (the precision of the balls fabrication shall be higher than the spatial resolution of the digital X-ray apparatus). Determination of the calibration data of the regular component of mechanical instability of X-ray apparatus is executed in compliance with the first variant of the invention, although the X-direction and Y-direction calibration data are determined using the projection of the ball of lower diameter, and the scale calibration data are determined by the projection of the ball of higher diameter. Using the second variant of the invention, the calibration precision is improved in comparison to the first variant. That is better manifested when calibrating X-ray apparatus with detector of higher spatial resolution. It is explained by the fact that, when using the first variant of the invention for calibration of X-ray apparatus with good spatial resolution, the X-direction and Y-direction calibration error increases, because the deviation of the projection of centre of the ball from the centre of projection of the ball becomes more "visible" for the detector, and the higher is the diameter of the X-ray contrast ball, the higher this deviation is. On the other hand, the higher is the diameter of the calibration X-ray contrast ball, the higher is the precision of scale calibration of the apparatus.

Thus, when using the calibration method under application for mechanical instability of the X-ray apparatus, digital detector of which has relatively low spatial resolution it is possible, in order to achieve the said technical result, to use the first variant of the invention. In case of using the calibration method under application for mechanical instability of the X-ray apparatus, digital detector of which has good spatial resolution, it is necessary to use the second variant of the invention.

Industrial application. Realization of X-ray images correction using the calibration data obtained by the method variants under application is explained by the flow scheme in FIG. 6 and may be implemented using the known technical facilities. Application of the calibration data obtained according to the first and the second methods improves low-contrast and high-contrast resolution of X-ray apparatus, owing to what, for example, in the medical X-ray diagnostics it is possible to detect the malignant neoplasms at an earlier stage. Implementation of the methods under application allows reducing of requirements to the mechanical precision of X-ray apparatus stand rotation together with simultaneous improvement of quality of the reconstructed images using calibration of mechanical instability of X-ray computed tomograph.

While this invention has been particularly shown and described with references to preferred embodiments thereof, it will be understood by those skilled in the art that various changes in form and details may be made therein without departing from the scope of the invention encompassed by the appended claims.

What is claimed is:

1. A calibration method of a digital X-ray apparatus, comprising:
    placing at least one X-ray contrast ball into a scanning field outside of a center of the scanning field;
    obtaining images of the scanning field;
    using coordinates of the center of a projection of the ball to determine regular components of a mechanical instability of the digital X-ray apparatus stand along an X-direction and a Y-direction;
    using a diameter of the projection of the ball to determine a scale regular component of the mechanical instability of the digital X-ray apparatus stand; and
    forming a calibration data set for the mechanical instability of the stand.

2. A calibration method of a digital X-ray apparatus, comprising:
    placing at least two X-ray contrast balls of different diameters into a scanning field of the apparatus outside of a centre of the scanning field;
    obtaining images of the scanning field;
    using coordinates of the center of a projection of a smaller ball to determine regular components of a mechanical instability of the digital X-ray apparatus stand along an X-direction and a Y-direction;
    using a diameter of the projection of a larger ball to determine a scale regular component of the mechanical instability of the digital X-ray apparatus stand; and
    forming a calibration data set for the mechanical instability of the stand.

* * * * *